United States Patent
Baraldi et al.

[11] Patent Number: 5,935,964
[45] Date of Patent: Aug. 10, 1999

[54] 1,2,4-TRIAZOLO[1,5-C] PYRIMIDINE HETEROCYCLIC ANALOGUES HAVING ANTAGONISTIC ACTIVITY ON ADENOSINE $A_{2A}$ RECEPTOR

[75] Inventors: Pier Giovanni Baraldi; Barbara Cacciari, both of Ferrara; Monica Valeria Angela Viziano, Milan; Silvio Dionisotti, Brugherio; Ennio Ongini, Segrate, all of Italy

[73] Assignee: Schering Corporation, Kenilworth, N.J.

[21] Appl. No.: 09/000,066

[22] PCT Filed: Jul. 2, 1996

[86] PCT No.: PCT/EP96/02881

§ 371 Date: Jan. 22, 1998

§ 102(e) Date: Jan. 22, 1998

[87] PCT Pub. No.: WO97/05138

PCT Pub. Date: Feb. 13, 1997

[30] Foreign Application Priority Data

Jul. 28, 1995 [IT] Italy .................. MI95A0167

[51] Int. Cl.[6] ............... A61K 31/505; C07D 487/14
[52] U.S. Cl. ........................... 514/267; 544/251
[58] Field of Search .................. 544/251; 514/267

[56] References Cited

U.S. PATENT DOCUMENTS 5,565,460  10/1996  Suzuki et al. ..................... 514/259

FOREIGN PATENT DOCUMENTS 9501356  1/1995  WIPO .

OTHER PUBLICATIONS

*Protective Groups in Organic Synthesis* by Theodora Greene pp. 10–11, 13, 29, 72–73 (1981).
*Protective Groups in Organic Chemistry* by J.F.W. McOmie pp. 145–147, 157–159 (1973).
*Pharmacol. Rev.* 46 (1994) pp. 143–156, Fred Holm et al.
*J. Pharmacol. Exp. Ther.*, 251 (1989) pp. 888–893, Jarvis et al.
*J. Med. Chem.*, 36 (1993) pp. 3731–3733, Nonaka et al.
*Bioorg. Med. Chem. Lett.*, 4 (1994) pp. 2539–2544, Baraldi et al.
*Progress Cardiovasc. Dis.*, 32 (1989), pp. 73–97, Belardinelli et al.
*Drug Dev. Res.*, 28 (1993), pp. 381–385, Schiffmann et al.
*J. Med. Chem.*, 35 (1992), pp. 407–422, Jacobson et al.
*Proc. Natl. Acad. Sci.—USA*, 77 (1980), pp. 5547–5551, Bruns et al.
*Br. J. Pharmacol.*, 78 (1983), pp. 207–212, Collis.

Primary Examiner—Emily Bernhardt
Attorney, Agent, or Firm—Anita W. Magatti

[57] ABSTRACT

Disclosed are adenosine $A_{2a}$ receptor antagonists of the formula

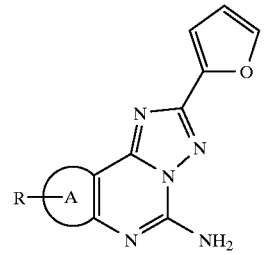

wherein A is pyrazole, imidazole or triazole ring;
R is

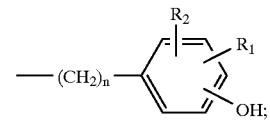

$R_1$ and $R_2$ are independently H, OH, halogen, alkoxy, alkyl, nitro, amino, CN, haloalkyl, haloalkoxy, carboxy or carboxamido; or the OH group together with one of $R_1$ or $R_2$, or $R_1$ and $R_2$ together, form a methylenedioxy group;
and n is 0–4;
said compounds are useful in the treatment of cardiovascular, central nervous system, and respiratory diseases.

9 Claims, No Drawings

1,2,4-TRIAZOLO[1,5-C] PYRIMIDINE HETEROCYCLIC ANALOGUES HAVING ANTAGONISTIC ACTIVITY ON ADENOSINE $A_{2A}$ RECEPTOR

The present invention relates to compounds having antagonistic activity on adenosine $A_{2a}$ receptors.

Adenosine is known to be an endogenous modulator of a number of physiological functions. At the cardiovascular system level, adenosine is a strong vasodilator and a cardiac depressor. On central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilatation at high doses. Adenosine acts as a lipolysis inhibitor on fat cells and as an antiaggregant on platelets (Stone T. W. Purine receptors and their pharmacological roles. In: Advances in drug research. Academic Press Limited, 1989, 18, 291–429; Progress Cardiovasc. Dis. 1989, 32, 73–97; Williams M., Adenosine and Adenosine receptors. The Humana Press, 1990).

Adenosine action is mediated by the interaction with different membrane specific receptors which belong to the family of receptors coupled with G proteins.

Biochemical and pharmacological studies, together with the recent acquirements in the molecular biology field, have up to now allowed to identify at least 4 different adenosine receptors: $A_1$, $A_{2a}$, $A_{2b}$, ed $A_3$ (Pharmacol. Rev., 1994, 46, 143–156).

Intense research efforts have made it possible to identify and develop analogs to adenosine able to interact as agonists with the $A_1$, $A_{2a}$ and $A_3$ receptors (Pharmacol. Rev., 1994, 46, 143–156).

The knowledge available on the physiological role of adenosine and its involvement in some pathological processes suggests that selective antagonists for the $A_{2a}$ receptor can be of pharmacological interest. At the level of the central nervous system, antagonistic $A_{2a}$ compounds could have antidepressive properties and stimulate the cognitive functions. Moreover, numerous data show that the $A_{2a}$ receptors are present in high density in the basal ganglia of which the importance in the control of movement is known. Hence, the hypothesis that $A_{2a}$ antagonists can improve motor-impairment due to neurodegenerative processes. Amongst these are included Parkinson's disease, senile dementia as in Alzheimer's disease and psychosis of organic origin (Drug Dev. Res., 1993, 28, 381–385).

At a peripheral level, $A_{2a}$ receptor antagonists could stimulate the respiratory functions and therefore have a therapeutic effect in the treatment of bronchospasm and, more generally, asthma. Moreover, with regard to the effects at a cardiovascular or renal level, an advantageous activity on renal flow can be envisaged and therefore the possibility of the treatment of renal insufficiency and of various cardiovascular disturbances.

Whilst some xanthine-structure have been known to be $A_1$ receptor selective antagonists (J Med. Chem., 1992, 35, 407–422), only recently novel xanthine (J. Med. Chem, 1993, 36, 3731–3733) and non-xanthine (PCT WO 9501356, published on Dec. 1, 1995, corresponding to Italian Patent application MI93A001396) Bioorg. Med. Chem. Lett, 1994, 4, 2539–2544) have been found to have high $A_{2a}$ affinity and moderate $A_{2a}$ vs $A_1$ selectivity (about 50-fold).

The compounds disclosed in WO 9501356 are 1,2,4-triazolo[1,5-c]pyrimidine heterocyclic analogues, on the heterocyclic ring of which is present, inter alia, an aryl group, particularly phenyl or phenylalkyl, optionally substituted with halogen atoms, $C_1$–$C_4$ alkoxy, $C_1$–$C_4$ alkyl, nitro, amino, cyano, $C_1$–$C_4$ haloalkyl, $C_1$–$C_4$ haloalkoxy, carboxy, carboxamido groups.

Moreover, it has surprisingly been found that the presence of at least one hydroxyl on the phenyl ring gives the compounds disclosed in WO9501356 an increased $A_{2a}$ selectivity.

Therefore, the present invention relates to compounds of general formula I:

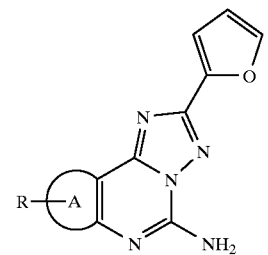

wherein:

A is a pyrazole, imidazole or triazole ring

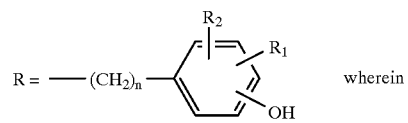

$R_1$ and $R_2$, which are the same or different, are H, OH, halogen, $C_1$–$C_4$ alkoxy, $C_1$–$C_4$ alkyl, nitro, amino, cyano, $C_1$–$C_4$ haloalkyl, $C_1$–$C_4$ haloalkoxy, carboxy, carboxamido groups; moreover the OH group, together with one of $R_1$ or $R_2$, or $R_1$ and $R_2$, can form the methylenedioxy group —O—$CH_2$—O—;

n is an integer from 0 to 4.

The invention also comprises the pharmaceutically acceptable salts of the compounds of general formula I.

The possible meanings of A can be represented by the following structural formulae:

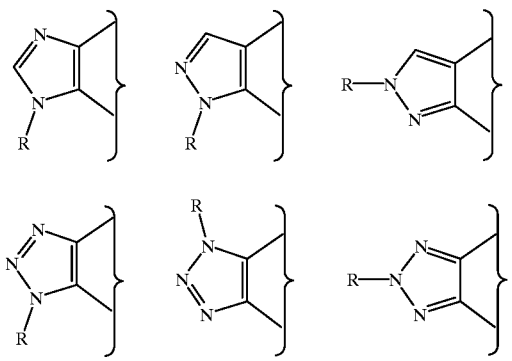

Examples of $C_1$–$C_4$ alkyl groups include methyl, ethyl, propyl, isopropyl, butyl and isobutyl.

Examples of $C_1$–$C_4$ alkoxy groups are methoxy, ethoxy, propoxy, isopropoxy, butoxy, tert-butoxy.

Halogen atoms are fluorine, chlorine, bromine, iodine.

Examples of $C_1$–$C_4$ groups haloalkyl are trifluoromethyl, 2-fluoroethyl, 2-chloroethyl.

Examples of $C_1$–$C_4$ haloalkoxy groups are trifluoromethoxy chloromethoxy, 2-fluoroethoxy, 2-chloroethoxy, 2,2,2-trifluoroethoxy.

Preferred compounds of formula I are those wherein A is pyrazolo[4,3-e] or 1,2,3-triazolo[5,4-e].

Particularly preferred compounds of formula I are those wherein A is pyrazolo[4,3-e], n ranges from 1 to 4 included, preferably 2 or 3, the OH group on the phenyl ring is at the para position and $R_1$ and $R_2$ are hydrogen.

A second group of particularly preferred compounds of formula I are those wherein A is pyrazolo[4,3-e], n is from 1 to 3, preferably 1 or 2, the OH group on the phenyl ring is at the meta position and $R_1$ and $R_2$ are hydrogen.

A third group of particularly preferred compounds of formula I are those wherein A is pyrazolo[4,3-e], n is from 1 to 4, preferably 2 or 3, the OH group on the phenyl ring is at the para position, $R_1$ is methoxy, preferably at the meta position, $R_2$ is hydrogen.

A fourth group of particularly preferred compounds of formula I are those wherein A is pyrazolo[4,3-e], n is from 1 to 4, preferably 2 or 3, the OH group on the phenyl ring is at the para position, $R_1$ is hydroxy, preferably at the meta position, $R_2$ is hydrogen.

A fifth group of particularly preferred compounds of formula I are those wherein A is 1,2,3-triazolo[5,4 -e], n is from 1 to 4, preferably 2 or 3, and the OH group on the phenyl ring can be at all the possible positions.

Particularly preferred are the following compounds:
5-amino-7-[β-(4-hydroxy-3-methoxy)-phenylethyl]-2-(2-furyl)-pyrazolo[4,3-e]-1,2,4-triazolo[1,5-c]pyrimidine;
5-amino-7-[β-(3-hydroxy)-phenylethyl]-2-(2-furyl)-pyrazolo[4,3-e]-1,2,4-triazolo[1,5-c]pyrimidine;
5-amino-7-[β-(2-hydroxy)-phenylethyl]-2-(2-furyl)-pyrazolo[4,3-e]-1,2,4-triazolo[1,5-c]pyrimidine;
5-amino-7-[γ-(4-hydroxy)-phenylpropyl]-2-(2-furyl)-pyrazolo[4,3-e]1,2,4-triazolo[1,5-c]pyrimidine;
5-amino-7-[4-hydroxybenzyl]-2-(2-furyl)-pyrazolo[4,3-e]-1,2,4-triazolo[1,5-c]pyrimidine;
5-amino-7-[β-(3,4-dihydroxy)-phenylethyl]-2-(2-furyl)-pyrazolo[4,3-e]-1,2,4-triazolo[1,5-c]pyriidine;
5-amino-8-[β-(4-hydroxy)-phenylethyl]-2-(2-furyl)-pyrazolo[4,3-e]-1,2,4-triazolo[1,5-c]pyrimidine;
5-amino-8-[γ-(4-hydroxy)-phenylpropyl]-2-(2-furyl)-pyrazolo[4,3-e]-1,2,4-triazolo[1,5-c]pyrimidine;
5-amino-8-[β-(3,4-dihydroxy)-phenylethyl]-2-(2-furyl)-pyrazolo[4,3-e]-1,2,4-triazolo[1,5-c]-pyrimidine;
5-amino-8-[β-(3,4-methylenedioxy)-phenylethyl]-2-(2-furyl)-pyrazolo[4,3-e]-1,2,4-triazolo[1,5-c]pyrimidine;
5-amino-8-(4-hydroxybenzyl)-2-(2-furyl)-pyrazolo[4,3-e]-1,2,4-triazolo[1,5-c]pyrimidine;
5-amino-7-[β-(4-hydroxy)-phenylethyl]-2-(2-furyl)-1,2,3-triazolo[5,4-e]-1,2,4-triazolo[1,5-c]-pyrimidine;
5-amino-7-[β-(4-hydroxy-3-iodo)-phenylethyl]-2-(2-furyl)-1,2,3-triazolo[5,4-e]-1,2,4-triazolo[1,5-c]-pyrimidine;
5-amino-7-[γ-(4-hydroxy)-phenylpropyl]-2-(2-furyl)-1,2,3-triazolo[5,4-e]-1,2,4-triazolo[1,5-c]-pyrimidine;
5-amino-7-[γ-(4-hydroxy-3-iodo)-phenylpropyl]-2-(2-furyl)-1,2,3-triazolo[5,4-e]-1,2,4-triazolo[1,5-c]pyrimidine;
5-amino-7-[β-(3,4-dihydroxy)-phenylpropyl]-2-(2-furyl)-1,2,3-triazolo[5,4-e]-1,2,4-triazolo[1,5-c]-pyrimidine;
5-amino-7-[β-(3,4-methylenedioxy)-phenylethyl]-2-(2-furyl)-1,2,3-triazolo[5,4-e]-1,2,4-triazolo[1,5-c]-pyrimidine; m.p 210–211° C.;
5-amino-8-[β-(4-hydroxy)-phenylethyl]-2-(2-furyl)-1,2,3-triazolo[5,4-e]-1,2,4-triazolo[1,5-c]-pyrimidine;
5-amino-8-[γ-(4-hydroxy)-phenylpropyl]-2-(2-furyl)-1,2,3-triazolo[5,4-e]-1,2,4-triazolo[1,5-c]-pyrimidine;
5-amino-8-[β-(3,4-dihydroxy)-phenylethyl]-2-(2-furyl)-1,2,3-triazolo[5,4-e]-1,2,4-triazolo[1,5-c]-pyrimidine;
5-amino-8-[β-(3,4-methylenedioxy)-phenylethyl]-2-(2-furyl)-1,2,3-triazolo[5,4-e]-1,2,4-triazolo[1,5-c]-pyrimidine;
5-amino-7-[β-(4-hydroxy-3-iodo)-phenylethyl]-2-(2-furyl)-pyrazolo[4,3-e]-1,2,4-triazolo[1,5-c]-pyrimidine;
5-amino-7-[γ-(4-dihydroxy-3-iodo)-phenylpropyl]-2-(2-furyl)-pyrazolo[4,3-e]-1,2,4-triazolo[1,5-c]-pyrimidine;
5-amino-7-[β-(3,4-methylenedioxy)-phenylethyl]-2-(2-furyl)-pyrazolo[4,3-e]-1,2,4-triazolo[1,5-c]-pyrimidine;

The compounds according to the present invention are prepared with known processes, in particular they are according to the processes described in WO Application 9501356.

Since in all the intermediates for the synthesis of the compounds of Formula I at least one OH group is present on the phenyl ring, to protect the OH group(s), during the various synthetic steps. The final compounds of formula I are thus obtained by deprotecting the phenyl OH group(s) once the complete structure has been obtained. Protection methods are conventionally known, for example as described in T. W. Greene, P. G. M. Woots, Protective Groups in Organic Synthesis, J. Wiley. N.Y. 1991, 2nd Edition.

A preferred protection method is the benzylation and following debenzylation on Pd/C in tetrahydrofuran. Alternatively, the protection method involves the use of the allyl group or, when two adjacent hydroxy groups are present, the methylendioxy group.

Therefore, another object of the present invention is a process for the preparation of compounds of formula (I), as reported above, which comprises the deprotection of the phenyl hydroxy groups of the compounds of formula (Ia)

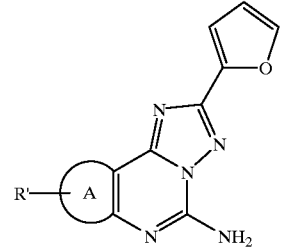

(Ia)

wherein:
A is as defined in formula (I);

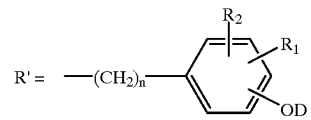

wherein D is a suitable protective group, preferably benzyl or allyl (or —$CH_2$— as protective group of two adjacent hydroxyl groups), $R_1$ and $R_2$, which are the same or different, are hydrogen, OD, wherein D is as defined above, a halogen atom, $C_1$–$C_4$ alkyl, nitro, amino, cyano, $C_1$–$C_4$ halogen alkoxy, carboxy, carboxamido group; n is as above defined.

The process according to the present invention also comprises the optional transformation of the obtained compound into a pharmaceutically acceptable salt.

BIOLOGICAL ACTIVITY

The pharmacological properties of the disclosed compounds were studied in the most sensitive and suitable experimental models both in vitro and in vivo.

The compounds of general formula I have advantageous properties of selectivity for the $A_{2a}$ receptor compared with those described in the above cited WO 9501356.

Adenosine $A_{2a}$ receptor affinity was tested by means of receptor binding techniques on bovine and rat (Sprague-Dawley strain), cerebellar corpus striatum, which is a tissue rich in $A_{2a}$ receptors. Compound $^3$H-CGS 21680 (J. Pharm. Exp. Ther. 1989, 251, 888–893) was used as the radioligand. The $A_1$ receptor affinity was tested with receptor binding techniques on bovine and rat (Sprague-Dawley strain), cerebellar cortex membranes, which is a tissue rich in $A_1$ receptors. $^3$H-Cyclohexyl-adenosine, $^3$H-CHA (Proc. Natl. Acad. Sci.—USA—1980, 77, 5547–5551) was used as the radioligand. The selectivity for the $A_{2a}$ receptor was evaluated from the comparison between the affinities for the $A_1$ or $A_{2a}$ receptor shown by each compound. A number of experimental data support the evidence that a marked relationship exists between the affinity found with binding techniques in brain tissues and the physiological effects modulated by adenosine receptors.

$A_{2a}$ receptors are mainly present in the vascular system and the stimulation thereof causes vasodilation. Therefore, the $A_{2a}$ antagonistic activity of these molecules has been studied by evaluating the capability of inhibiting vasodilation induced by adenosine agonists in vascular tissues such as rat aorta and bovine or porcine coronary arteries.

These compounds were unable to antagonize negative chronotropic effects induced by $A_1$ receptor agonists when tested on isolated rat atria (Br. J. Pharmacol., 1983, 78, 207–212).

Another test to evaluate the antagonistic activity of the new compounds is the study of platelet aggregation. In fact, adenosine or the analogues thereof are known to inhibit platelet aggregation induced by different aggregatory agents, among which ADP. Therefore, the capability of the novel compounds of antagonizing the inhibitory effect induced by NECA or CGS 21680 agonists was tested using rabbit platelets.

This test is particularly important as only the $A_{2a}$ receptor is present on platelet cell membranes.

The in vivo activity was evaluated in Swiss mice and spontaneously hypertensive rats (SHR). The behavioural response to a treatment with different doses of the tested compounds administered parenterally was evaluated in the mice. In the SHR rats, the tested compounds were administered parenterally at increasing doses and the capability thereof of antagonizing the bradycardic and hypotensive effects induced by $A_1$ and $A_{2a}$ receptor agonists, respectively, was measured.

A number of the compounds of formula I showed a marked $A_{2a}$ affinity with Ki ranging from 1 to 10 nM. The $A_{2a}$ selectivity for some compounds is 200–800fold, which is markedly higher than that of the compounds known up to now.

In the platelet aggregation test, said compounds proved to effectively block the antiaggregatory effects induced by $A_{2a}$ agonists, with pA$_2$ values ranging from 8 to 10.

The compounds of the invention antagonize in a variety of vascular districts, with a similar potency, vasodilatation mediated by $A_{2a}$ receptors, whereas they are not able of blocking the negative chronotropic effect induced by $A_1$ agonists in rat isolated atria. In the in vivo models, the tested compounds showed a poor stimulating activity on central nervous system, they antagonized the hypotension induced by $A_{2a}$ agonists without changing significantly the heart rate. The compounds turned out to be active at doses from 0.001 to 3 mg/kg intraperitoneally.

For the envisaged therapeutical uses, compounds I will be formulated as suitable pharmaceutical compositions, which can be administered, for example, by the oral, parenteral or transdermal routes, using known techniques and excipients, as described for example in Remington's Pharmaceutical Sciences Handbook, Mack Pub. Co., NY, USA, XVII ed. Said compositions are comprised within the scope of the present invention.

The daily dosage will depend, of course, on many factors (severity of the pathology to treat, patient conditions, toxicology and pharmacokinetic of the selected compound) but generally it will range from 0.01 to 10 mg/kg body weight, preferably from 0.1 to 1 mg/kg, optionally subdivided in more administrations. Examples of pharmaceutical compositions comprise capsules, tablets, solutions, syrups, vials, controlled-release forms, transdermal forms (patches) and the like.

The following examples further illustrate the invention.

EXAMPLE 1

5-amino-7-[β-(4-hydroxy)-phenylethyl]-2-(furyl)-pyrazolo[4,3-e]-1,2,4-triazolo[1,5-c]pyrimidine A solution of 5-amino-7-[β-(4-benzyloxy)-phenylethyl]-2-(2-furyl)-pyrazolo[4,3-e]-1,2,4-triazolo-[1,5-c]pyrimidine (1.5 g; 0.003 moles) in THF (20 ml) is added with HCOONH$_4$ (0.81 g, 0.012 moles) and 10% C-Pd (0.3 g) and refluxed for 2 hours. When the reaction is complete, the catalyst is filtered off and the supernatant is concentrated. The residue is chromatographed (AcOEt) to give 0.44 (41%) of the desired compound, which is a white solid, m.p. 265 (dec.). IR (KBr) cm$^{-1}$: 3500–3100. 1650. 1610. 1525, 1435; $^1$H NMR (DMSO) δ: 3.04, (t, 2H, J=8 Hz); 4.41 (t, 2H, J=8 Hz); 6.60 (d, 2H, J=8 Hz); 6.73–6.74 (m, 1H); 6.93 (d, 2H, J=8); 7.22 (d, 1H, J=4 Hz); 7.94 (s, 1H); 8.07 (bs, 2H); 8.16 (s, 1H), 9.22 (s, 1H).

EXAMPLE 2

0.25 ml of an 1M BCl$_3$ solution in CH$_2$Cl$_2$ were added at 0° C. to a solution of 50 mg (0.12 mmol) of 5-amino-7[β-(3,4-methylenedioxy)phenylethyl]-2-(2-furyl)-pyrazole-[4,3-e]-1,2,4-triazole-[1,5-c]-pyrimidine.

The mixture was left at 4° C. for 5 h. 1 ml of methanol was added and the solvent was evaporated, to give 33 mg of the corresponding 3,4-dihydroxy derivative (m.p. 272° dec.).

EXAMPLE 3

Following the same procedures of Example 1 or 2, starting from the suitable benzyloxy- or methylendioxy-substituted precursors, the following compounds were obtained:

5-amino-7-[β-(4-hydroxy-3-methoxy)-phenylethyl]-2-(2-furyl)-pyrazolo[4,3-e]-1,2,4-triazolo[1,5-c]pyrimidine;

5-amino-7-[β-(3-hydroxy)-phenylethyl]-2-(2-furyl)-pyrazolo[4,3-e]-1,2,4-triazolo[1,5-c]pyrimidine;

5-amino-7-[β-(2-hydroxy)-phenylethyl]-2-(2-furyl)-pyrazolo[4,3-e]-1,2,4-triazolo[1,5-c]pyrimidine;

5-amino-7-[γ-(4-hydroxy)-phenylpropyl]-2-(2-furyl)-pyrazolo[4,3-e]1,2,4-triazolo[1,5-c]pyrimidine; m.p 189–191° C.;

5-amino-7-[4-hydroxybenzyl]-2-(2-furyl)-pyrazolo[4,3-e]-1,2,4-triazolo[1,5-c]pyrimidine, m.p.>280° C.;

5-amino-8-[β-(4-hydroxy)-phenylethyl]-2-(2-furyl)-pyrazolo[4,3-e]-1,2,4-triazolo[1,5-c]pyrimidine;

5-amino-8-[γ-(4-hydroxy)-phenylpropyl]-2-(2-furyl)-pyrazolo[4,3-e]-1,2,4-triazolo[1,5-c]pyrimidine;

5-amino-8-[β-(3,4-dihydroxy)-phenylethyl]-2-(2-furyl)-pyrazolo[4,3-e]-1,2,4-triazolo[1,5-c]-pyrimidine;
5-amino-8-[β-(3,4-methylenedioxy)-phenylethyl]-2-(2-furyl)-pyrazolo[4,3-e]-1,2,4-triazolo[1,5-c]pyrimidine;
5-amino-8-(4-hydroxybenzyl)-2-(2-furyl)-pyrazolo[4,3-e]-1,2,4-triazolo[1,5-c]pyrimidine;
5-amino-7-[β-(4-hydroxy)-phenylethyl]-2-(2-furyl)-1,2,3-triazolo[5,4-e]-1,2,4-triazolo[1,5-c]-pyrimidine;
5-amino-7-[β-(4-hydroxy-3-iodo)-phenylethyl]-2-(2-furyl)-1,2,3-triazolo[5,4-e]-1,2,4-triazolo[1,5-c]-pyrimidine;
5-amino-7-[γ-(4-hydroxy)-phenylpropyl]-2-(2-furyl)-1,2,3-triazolo[5,4-e]-1,2,4-triazolo[1,5-c]-pyrimidine;
5-amino-7-[γ-(3,4-dihydroxy)-phenylpropyl]-2-(2-furyl)-1,2,3-triazolo[5,4-e]-1,2,4-triazolo[1,5-c]-pyrimidine; m.p.204–206° C.;
5-amino-7-[γ-(3,4-methylendioxy)-phenylpropyl]-2-(2-furyl)-1,2,3-triazolo[5,4-e]-1,2,4-triazolo[1,5-c]-pyrimidine; m.p 210–211° C.;
5-amino-7-[γ-(4-hydroxy-3-iodo)-phenylpropyl]-2-(2-furyl)-1,2,3-triazolo[5,4-e]-1,2,4-triazolo[1,5-c]-pyrimidine;
5-amino-7-[β-(3,4-dihydroxy)-phenylethyl]-2-(2-furyl)-1,2,3-triazolo[5,4-e]-1,2,4-triazolo[1,5-c]-pyrimidine;
5-amino-7-[β-(3,4-methylenedioxy)-phenylethyl]-2-(2-furyl)-1,2,3-triazolo[5,4-e]-1,2,4-triazolo[1,5-c]-pyrimidine;
5-amino-8-[β-(4-hydroxy)-phenylpropyl]-2-(2-furyl)-1,2,3-triazolo[5,4-e]-1,2,4-triazolo[1,5-c]-pyrimidine;
5-amino-8-[γ-(4-hydroxy)-phenylpropyl]-2-(2-furyl)-1,2,3-triazolo[5,4-e]-1,2,4-triazolo[1,5-c]-pyrimidine;
5-amino-8-[β-(3,4-dihydroxy)-phenylethyl]-2-(2-furyl)-1,2,3-triazolo[5,4-e]-1,2,4-triazolo[1,5-c]-pyrimidine;
5-amino-8-[β-(3,4-methylenedioxy)-phenylethyl]-2-(2-furyl)-1,2,3-triazolo[5,4-e]-1,2,4-triazolo[1,5-c]-pyrimidine;
5-amino-7-[β-(4-hydroxy-3-iodo)-phenylethyl]-2-(2-furyl)-pyrazolo[4,3-e]-1,2,4-triazolo[1,5-c]-pyrimidine;
5-amino-7-[γ-(4-hydroxy-3-iodo)-phenylpropyl]-2-(2-furyl)-pyrazolo[4,3-e]-1,2,4-triazolo[1,5-c]-pyrimidine;
5-amino-7-[β-(3,4-methylenedioxy)-phenylethyl]-2-(2-furyl)-pyrazolo[4,3-e]-1,2,4-triazolo[1,5-c]-pyrimidine.

We claim:

1. Compounds of general formula (I)

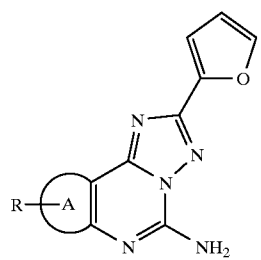

I wherein:
A is a pyrazole, imidazole or triazole ring

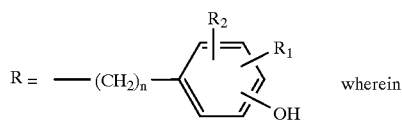

$R_1$ and $R_2$, which are the same or different, are H, OH, halogen, $C_1$–$C_4$ alkoxy, $C_1$–$C_4$ alkyl, nitro, amino, cyano, $C_1$–$C_4$ haloalkyl, $C_1$–$C_4$ haloalkoxy, carboxy, carboxamido groups; moreover the OH group, together with one of $R_1$ or $R_2$, or $R_1$ and $R_2$, can form the methylenedioxy group —O—$CH_2$—O—;
n is an integer from 0 to 4,
or the pharmaceutically acceptable salts thereof.

2. Compounds according to claim 1, wherein A is a group selected from

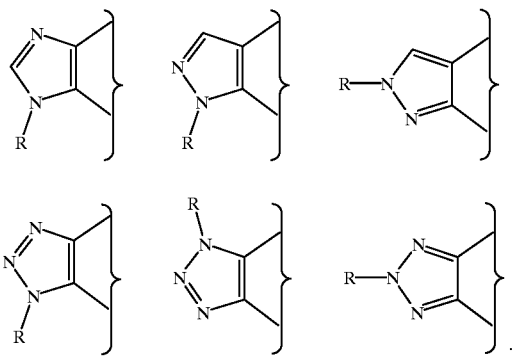

3. Compounds according to claim 1, wherein A is pyrazolo, n is from 1 to 4, the OH group on the phenyl ring is at the para position and $R_1$ and $R_2$ are hydrogen.

4. Compounds according to claim 1, wherein A is pyrazolo, n is from 1 to 4, the OH group on the phenyl ring is at the meta position and $R_1$ and $R_2$ are hydrogen.

5. Compounds according to claim 1, wherein A is pyrazolo, n is from 1 to 4, the OH group on the phenyl ring is at the para position, $R_1$ is methoxy, preferably at the meta position, $R_2$ is hydrogen.

6. Compounds according to claim 1, wherein A is pyrazolo, n is from 1 to 4, the OH group on the phenyl ring is at the para position, $R_1$ is hydroxy, preferably at the meta position, $R_2$ is hydrogen.

7. Compounds according to claim 1, wherein A is 1,2,3-triazolo, n is from 1 to 4, and the OH group on the phenyl ring can be at all the possible positions.

8. A compound according to claim 1, selected from the group consisting of:
5-amino-7-[β-(4-hydroxy-3-methoxy)-phenylethyl]-2-(2-furyl)-pyrazolo[4,3-e]-1,2,4-triazolo[1,5-c]pyrimidine;
5-amino-7-[β-(3-hydroxy)-phenylethyl]-2-(2-furyl)-pyrazolo[4,3-e]-1,2,4-triazolo[1,5-c]pyrimidine;
5-amino-7-[β-(2-hydroxy)-phenylethyl]-2-(2-furyl)-pyrazolo[4,3-e]-1,2,4-triazolo[1,5-c]pyrimidine;
5-amino-7-[γ-(4-hydroxy)-phenylpropyl]-2-(2-furyl)-pyrazolo[4,3-e]1,2,4-triazolo[1,5-c]pyrimidine;
5-amino-7-[4-hydroxybenzyl]-2-(2-furyl)-pyrazolo[4,3-e]-1,2,4-triazolo[1,5-c]pyrimidine;
5-amino-8-[β-(4-hydroxy)-phenylethyl]-2-(2-furyl)-pyrazolo[4,3-e]-1,2,4-triazolo[1,5-c]pyrimidine;
5-amino-8-[γ-(4-hydroxy)-phenylpropyl]-2-(2-furyl)-pyrazolo[4,3-e]-1,2,4-triazolo[1,5-c]pyrimidine;
5-amino-8-[β-(3,4-dihydroxy)-phenylethyl]-2-(2-furyl)-pyrazolo[4,3-e]-1,2,4-triazolo[1,5-c]-pyrimidine;
5-amino-8-[β-(3,4-methylenedioxy)-phenylethyl]-2-(2-furyl)-pyrazolo[4,3-e]-1,2,4-triazolo[1,5-c]pyrimidine;
5-amino-8-(4-hydroxybenzyl)-2-(2-furyl)-pyrazolo[4,3-e]-1,2,4-triazolo[1,5-c]pyrimidine;
5-amino-7-[β-(4-hydroxy)-phenylethyl]-2-(2-furyl)-1,2,3-triazolo[5,4-e]-1,2,4-triazolo[1,5-c]-pyrimidine;
5-amino-7-[β-(4-hydroxy-3-iodo)-phenylethyl]-2-(2-furyl)-1,2,3-triazolo[5,4-e]-1,2,4-triazolo[1,5-c]-pyrimidine;

5-amino-7-[γ-(4-hydroxy)-phenylpropyl]-2-(2-furyl)-1,2,3-triazolo[5,4-e]-1,2,4-triazolo[1,5-c]-pyrimidine;

5-amino-7-[γ-(3,4-dihydroxy)-phenylpropyl]-2-(2-furyl)-1,2,3-triazolo[5,4-e]-1,2,4-triazolo[1,5-c]-pyrimidine;

5-amino-7-[γ-(3,4-methylendioxy)-phenylpropyl]-2-(2-furyl)-1,2,3-triazolo[5,4-e]-1,2,4-triazolo[1,5-c]-pyrimidine; m.p 210–211° C.;

5-amino-7-[γ-(4-hydroxy-3-iodo)-phenylpropyl]-2-(2-furyl)-1,2,3-triazolo[5,4-e]-1,2,4-triazolo[1,5-c]-pyrimidine;

5-amino-7-[β-(3,4-dihydroxy)-phenylethyl]-2-(2-furyl)-1,2,3-triazolo[5,4-e]-1,2,4-triazolo[1,5-c]-pyrimidine;

5-amino-7-[β-(3,4-methylenedioxy)-phenylethyl]-2-(2-furyl)-1,2,3-triazolo[5,4-e]-1,2,4-triazolo[1,5-c]-pyrimidine;

5-amino-8-[β-(4-hydroxy)-phenylpropyl]-2-(2-furyl)-1,2,3-triazolo[5,4-e]-1,2,4-triazolo[1,5-c]-pyrimidine;

5-amino-8-[γ-(4-hydroxy)-phenylpropyl]-2-(2-furyl)-1,2,3-triazolo[5,4-e]-1,2,4-triazolo[1,5-c]-pyrimidine;

5-amino-8-[β-(3,4-dihydroxy)-phenylethyl]-2-(2-furyl)-1,2,3-triazolo[5,4-e]-1,2,4-triazolo[1,5-c]-pyrimidine;

5-amino-8-[β-(3,4-methylenedioxy)-phenylethyl]-2-(2-furyl)-1,2,3-triazolo[5,4-e]-1,2,4-triazolo[1,5-c]-pyrimidine;

5-amino-7-[β-(4-hydroxy-3-iodo)-phenylethyl]-2-(2-furyl)-pyrazolo[4,3-e]-1,2,4-triazolo[1,5-c]-pyrimidine;

5-amino-7-[γ-(4-hydroxy-3-iodo)-phenylpropyl]-2-(2-furyl)-pyrazolo[4,3-e]-1,2,4-triazolo[1,5-c]-pyrimidine;

5-amino-7-[β-(3,4-methylenedioxy)-phenylethyl]-2-(2-furyl)-pyrazolo[4,3-e]-1,2,4-triazolo[1,5-c]-pyrimidine.

9. Pharmaceutical compositions containing as the active ingredient a therapeutically effective amount of a compound of the claim 1 in admixture with conventional carriers and excipients.

* * * * *